US006308750B1

(12) United States Patent  
Burke

(10) Patent No.: US 6,308,750 B1  
(45) Date of Patent: Oct. 30, 2001

(54) MICROARRAYER APPARATUS

(75) Inventor: Julian Burke, Polegate (GB)

(73) Assignee: Genpak Limited, Brighton (GB)

( * ) Notice: Subject to any disclaimer, the term of this patent is extended or adjusted under 35 U.S.C. 154(b) by 0 days.

(21) Appl. No.: 09/541,078

(22) Filed: Mar. 31, 2000

(30) Foreign Application Priority Data

Jul. 20, 1999 (GB) .................................................. 99116931

(51) Int. Cl.[7] .............................. B65B 43/42; B67C 3/00
(52) U.S. Cl. .............................. 141/130; 141/83; 141/98; 422/68.1; 422/99
(58) Field of Search ............................. 141/130, 83, 85, 141/98; 422/68.1, 99, 100; 435/6

(56) References Cited

U.S. PATENT DOCUMENTS 5,541,064 * 7/1996 Bacus et al. .............................. 435/6

FOREIGN PATENT DOCUMENTS 0 113 075 7/1984 (EP) .  
0 798 550 A1 10/1997 (EP) .

* cited by examiner

Primary Examiner—Timothy L. Maust  
(74) Attorney, Agent, or Firm—Everett G. Diederiks, Jr.

(57) ABSTRACT

A manual microarrayer apparatus is disclosed which includes an integral visual magnification system alphanumeric counter and LED display for tracking samples in a microtitre plate. The apparatus is preferably reversible so as to provide left and right handed user formats.

18 Claims, 1 Drawing Sheet

MICROARRAYER APPARATUS

BACKGROUND OF THE INVENTION

1. Field of the Invention

The present invention relates to microarrayer apparatus, and in particular to a manually operable spotting station.

2. Discussion of the Prior Art

At the simplest level, a microarrayer is a system for transferring material from one location, the source, to a second location, the target. In practice, source material is usually biological material contained in a microtitre plate, and the target is either a glass microscope slide or nylon filter.

Microarrayers are used to spot DNA or other biological material onto glass slides or other rigid substrates. It is possible to produce microarrays using either an automated system or by hand.

Robotic systems have several advantages: they are fast and accurate and produce large numbers of identical arrays. They are, however, also relatively expensive from the point of view of initial purchase costs.

It is feasible to produce an array by hand if only a few slides, each with 200 different samples or less, are required. However, hand-spotting an array is only really practical with a feature pitch of approximately 1.0 mm (the feature pitch is the centre to centre distance between adjacent spots). Using a pitch of 1.0 mm and an 8×12 grid layout, which corresponds to a standard 96 well microtitre plate, allows up to 6 grids to be fitted on to a standard microscope slide. However, this does not leave much of a handling margin. Therefore, conventionally only two grids per slide are usually provided. Each grid can be different, or they can be duplicates. Because the most time-consuming element of producing an array is the cleaning cycle, it is common to work on several slides at the same time.

It is desired to provide apparatus to assist in producing microarrays which is substantially cheaper than fully automated systems and which enables an operator to produce a microarray more quickly, accurately and at a smaller pitch spacing than is conventionally possible using the naked eye.

SUMMARY OF THE INVENTION

According to a first aspect of the present invention there is provided a manually operable spotting station.

An advantage of the present invention is that more microarrays can be arranged on a single slide then is conventionally possible.

According to a second aspect of the present invention there is provided a manual microarrayer.

According to a third aspect of the present invention there is provided non-automated apparatus.

According to a fourth aspect of the present invention there is provided the combination.

According to a fifth aspect of the present invention there is provided a manually operable non-automated spotting station.

According to a sixth aspect of the present invention there is provided a manually operable non-automated spotting station for DNA analysis.

Various embodiments of the present invention will now be described, by way of example only, and with reference to the accompanying drawing.

DETAILED DESCRIPTION OF THE PREFERRED EMBODIMENT

Figure 1:
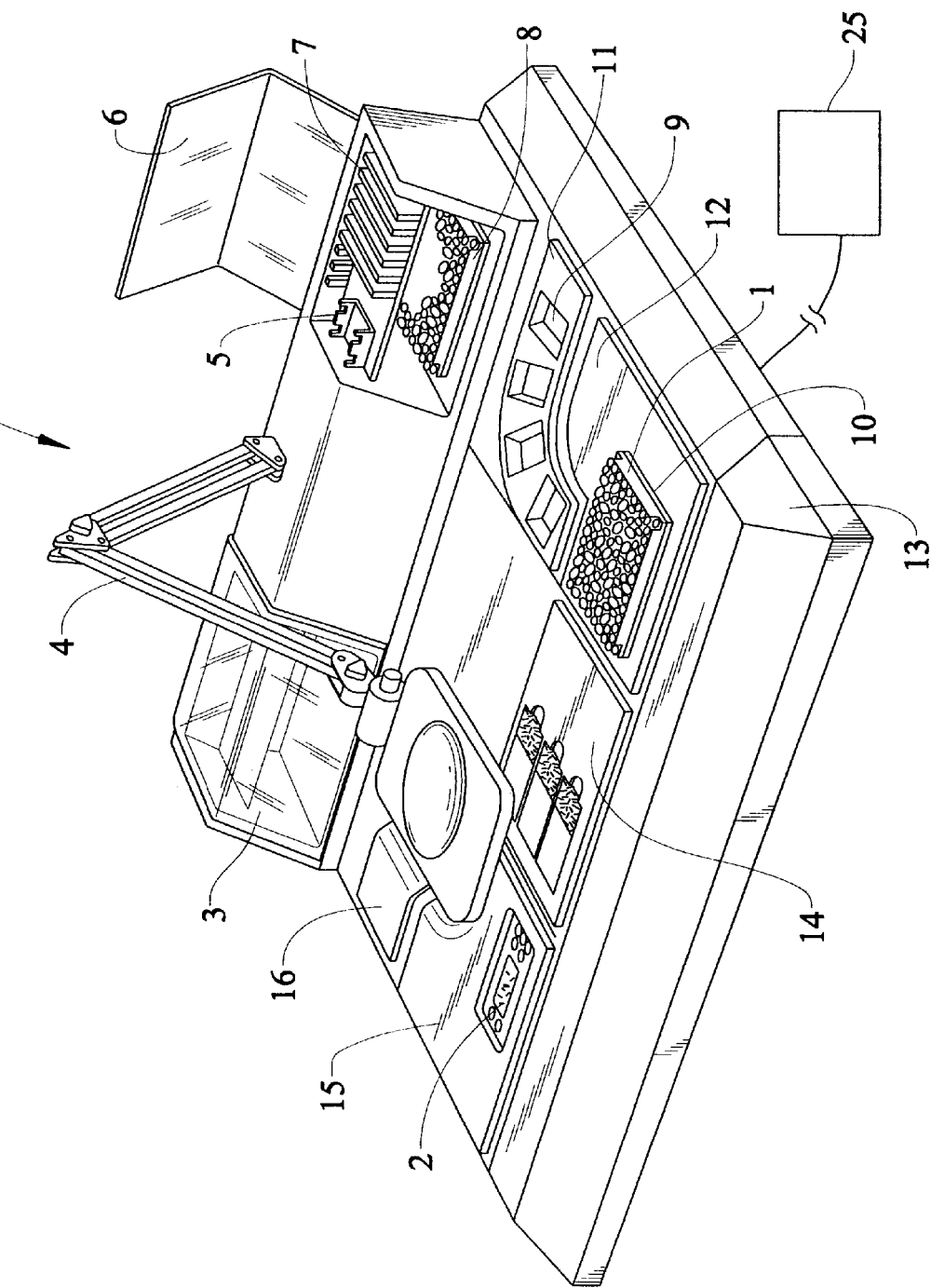
FIG. 1 shows a microarrayer system constructed in accordance with the present invention.

A microarrayer system 20 according to an embodiment of the present invention is shown in FIG. 1. The microarrayer 20 has a wash bath section 11, a sample tray section 12, a body section 13, a slide plate section 14, a counter section 15, and a fascia section 16.

The microarrayer 20 accommodates a sample tray 1 and has an integral sample well counter 2 (preferably alphanumeric), a storage compartment with a storage access lid 3 shown in a closed position, a magnification system 4, a pin storage area 5, a storage access lid 6, a slide storage area 7, a plate storage area 8, a wash bath 9. A reference frame 10 (indexed A–H, 1–12 or A–P, 1–24) is also preferably provided. Separate sheltered storage areas for clean and arrayed slides, as well as for spotting pins, are provided.

Each workstation preferably has a cleaning station consisting of 4 stainless steel or plastic trays (approx. 55×35×20 mm deep), a sample source holder for one or more microtitre plates (86×128 mm), a slide spotting area for 3 slides (total area 75×75 mm), a pin storage area for 40 to 75 mm long pins, an instrument rest (handle is approx. 10 mm diameter), a counter, and a stereo zoom microscope or an eyepieceless low magnification stereo spatial imaging system. The counter in one embodiment is capable of sequentially indicating 96 wells (A1 to H12) and/or 384 wells (A1 to P24), and can be reset at any time.

Various different pitch spacings can be achieved using the apparatus of the present invention. For reference, at a feature pitch of 1.0 mm, single copies of 96 samples will occupy an area 8×12 mm; at a feature pitch of 0.5 mm, single copies of 96 samples will occupy an area of 4×6 mm; and at a feature pitch of 0.2 mm, single copies of 96 samples will occupy an area of 1.4×2.2 mm.

The bench-top workstation according to the preferred embodiment has been designed to facilitate the production of hand spotted arrays. Preferably a stereo zoom microscope with an integral light source is provided which enables arrays pitched at e.g. 1.0 mm, 0.5 mm, 0.2 mm or less to be produced. The system preferably has a magnification within the range of ×5 to ×40 (with a conventional stereo zoom microscope) or ×2 to ×10 with an eyepieceless low magnification stereo spatial imaging system or viewer.

According to the preferred embodiment a stereo zoom microscope at six fold magnification is provided which enables 0.5 mm, 0.4 mm, 0.3 mm, and 0.2 mm or smaller pitch arrays to be produced. These formats enable many grids to be put on a single slide.

Grids may be laid with the aid of a template placed underneath the slide. This can be a piece of graph paper taped to the underside of the slide, an indexed printed grid, or an engraved stage similar to a microscope stage. According to another embodiment an indexed adhesive label is used for each slide. This provides a permanent means for identifying each sample within a grid. According to a particularly preferred embodiment, a grid template may be provided above the slide, and used as a guide for an operator.

Samples may be spotted out using a printing pin similar or substantially identical to those used in automated apparatus. Spots are produced by gently touching the pin down onto the slide surface. The first few spots should preferably be made onto a waste area, as they are inevitably uneven until excess sample material on the side of the pin has drained away.

To produce a circular spot the pin should be held as vertically as possible. If the angle is much less than 80° C., the spots will be oval. Pins should be touched down gently but firmly. If not, then the spots tend to end up comma shaped. The dwell time (how long the pin actually touches the surface) also affects the volume that is deposited. Too much sample results an uneven "cracked" spot or a doughnut effect. Neither such shapes are good for reading the array following hybridisation.

The effectiveness of the cleaning protocols can be checked using fluorescent dyes. The pin must be cleaned between successive samples. A simple 4-stage process is adequate. The pin is first touched down onto a blotting pad to remove sample material, then washed in distilled water and rinsed in 95% ethanol. Finally, the pin is dried by blotting onto a second pad. Following the completion of each set of slides, the pin is cleaned using ultrasound.

Sample material is colorless and dries almost instantly when spotted out, making it extremely easy for an operator to lose track of where he/she is. Accordingly, conventionally it has been problematic to keep track of which samples have been spotted out and of their locations within a microarray.

A particularly preferred embodiment includes a sample tracking device (preferably a LED display) and an alphanumeric counter which are provided to indicate to a user which wells of a microtitre plate have been sampled. This reduces the likelihood that samples will be over-spotted, omitted, or duplicated which is a very real problem with conventional track spotting techniques, and hence this preferred feature provides significant advantages over conventional techniques.

According to an embodiment, the following protocol is used:

1. using a sampling pin mounted in a holder, the operator collects a sample from the first well (A1) on a microtitre plate;
2. moving to the slide area, the first spot is made by placing the pin over the required position and "touching off" the sample onto the slide;
3. washing the sampling pin by: (a) blotting in a wash bath; (b) twice dipping into the wash bath; and then (c) blotting again in wash bath;
4. indexing the alphanumeric counter to indicate the next sample well (A2);
5. repeating cycle for the next sample well.

According to another preferred feature, the microarrayer may comprise a base platform and an upper platform on which all the elements are provided. The upper platform can be turned around so as to change the "handedness" of the apparatus and hence provide both left and right handed user formats.

What is claimed is:

1. A manually operable spotting station comprising:
    a body section;
    a cleaning station or wash bath integrally formed in said body section;
    means, mounted on said body section, for receiving a sample tray
    means, integrally formed in said body section, for receiving a slide; and
    a visual magnification system, mounted on said body section, for viewing a slide.
2. A manually operable spotting station as claimed in claim 1, further comprising a sample tracking device for indicating which wells of a microtitre plate have been sampled.
3. A manually operable spotting station as claimed in claim 2, wherein said sample tracking device comprises an array of LEDs.
4. A manually operable spotting station as claimed in claim 3, wherein said array of LEDs are arranged in a 8 ×12 or 16×24 format.
5. A manually operable spotting station as claimed in claim 2, wherein said sample tracking device is operated by a foot pedal.
6. A manually operable spotting station as claimed in claim 1, further comprising alphanumeric sample well counter integrally formed in said body section.
7. A manually operable spotting station as claimed in claim 1, wherein said visual magnification system provides at least a two-fold magnification.
8. A manually operable spotting station as claimed in claim 7, wherein said visual magnification system is a four-fold, six-fold, eight-fold or ten-fold magnification system.
9. A manually operable spotting station as claimed in claim 1, wherein said visual magnification system has a magnification selected from the group consisting of:
    (a) at least ×5; (b) at least ×10; (c) at least ×20; and
    (d) at least ×40.
10. A manually operable spotting station as claimed in claim 1, wherein said visual magnification system comprises a stereo zoom microscope.
11. A manually operable spotting station as claimed in claim 1, wherein said visual magnification system comprises a head-up display.
12. A manually operable spotting station as claimed in claim 1, further comprising an integral light source.
13. A manually operable spotting station as claimed in claim 12, wherein said light source is dichroic.
14. A manually operable spotting station as claimed in claim 1 further comprising a gridded template for guiding an operator.
15. A manually operable spotting station according to claim 14, wherein said spotting station further comprises an LED display near said sample tray reception means for indicating when a well of a sample tray has been used.
16. A manually operable spotting station according to 15, wherein said LED display is linked to an alphanumeric counter.
17. A manual microarrayer apparatus for assisting in the production of microarrays at a pitch spacing of 0.5 mm or smaller, comprising the following integral components:
    an imaging system;
    a light source;
    an alphanumeric counter; and
    a foot operated sample tracking device.
18. A manually operable non-automated spotting station for DNA analysis comprising:
    means for receiving a microtitre plate;
    an integral microscope for viewing a slide;
    an electronic display for displaying which well of a microtitre plate has had biological material removed therefrom and for displaying the current target position to be spotted on a slide; and
    a base section and an upper section, said upper section being reversible so as to provide both left and right handed user formats.

* * * * *